(12) United States Patent
Steinfeld et al.

(10) Patent No.: US 11,707,484 B2
(45) Date of Patent: Jul. 25, 2023

(54) FOOD SUPPLEMENT, USES THEREOF, METHOD FOR FOOD SUPPLEMENTATION, AND ORAL SPRAY

(71) Applicant: URSAPHARM ARZNEIMITTEL GMBH, Saarbrücken (DE)

(72) Inventors: Ute Steinfeld, St. Ingbert (DE); Dominik Holzer, St. Ingbert (DE)

(73) Assignee: URSAPHARM ARZNEIMITTEL GMBH, Saarbrücken (DE)

( * ) Notice: Subject to any disclaimer, the term of this patent is extended or adjusted under 35 U.S.C. 154(b) by 0 days.

(21) Appl. No.: 16/961,534

(22) PCT Filed: Jan. 14, 2019

(86) PCT No.: PCT/EP2019/050799
§ 371 (c)(1),
(2) Date: Jul. 10, 2020

(87) PCT Pub. No.: WO2019/138106
PCT Pub. Date: Jul. 18, 2019

(65) Prior Publication Data
US 2021/0052636 A1 Feb. 25, 2021

(30) Foreign Application Priority Data
Jan. 12, 2018 (DE) .................. 10 2018 200 492.7
Apr. 5, 2018 (DE) .................. 10 2018 205 160.7

(51) Int. Cl.
| | |
|---|---|
| *A61K 33/14* | (2006.01) |
| *A23L 29/00* | (2016.01) |
| *A23L 33/15* | (2016.01) |
| *A23L 33/29* | (2016.01) |
| *A61K 9/00* | (2006.01) |
| *A61K 9/08* | (2006.01) |
| *A61K 9/107* | (2006.01) |
| *A61K 31/19* | (2006.01) |
| *A61K 45/06* | (2006.01) |
| *A61K 47/14* | (2017.01) |
| *A61K 47/26* | (2006.01) |
| *A61K 47/44* | (2017.01) |
| *A61K 47/46* | (2006.01) |
| *A61K 31/355* | (2006.01) |
| *A61K 31/375* | (2006.01) |
| *A61K 31/4415* | (2006.01) |
| *A61K 31/51* | (2006.01) |
| *A61K 31/522* | (2006.01) |
| *A61K 31/525* | (2006.01) |

(52) U.S. Cl.
CPC ............ *A61K 33/14* (2013.01); *A23L 29/035* (2016.08); *A23L 33/15* (2016.08); *A23L 33/29* (2016.08); *A61K 9/006* (2013.01); *A61K 9/08* (2013.01); *A61K 9/1075* (2013.01); *A61K 31/19* (2013.01); *A61K 31/355* (2013.01); *A61K 31/375* (2013.01); *A61K 31/4415* (2013.01); *A61K 31/51* (2013.01); *A61K 31/522* (2013.01); *A61K 31/525* (2013.01); *A61K 45/06* (2013.01); *A61K 47/14* (2013.01); *A61K 47/26* (2013.01); *A61K 47/44* (2013.01); *A61K 47/46* (2013.01)

(58) Field of Classification Search
None
See application file for complete search history.

(56) References Cited

U.S. PATENT DOCUMENTS

| | | | | |
|---|---|---|---|---|
| 4,525,341 A | * | 6/1985 | Deihl | A61P 3/02 514/474 |
| 5,456,677 A | * | 10/1995 | Spector | A61M 35/003 128/200.14 |
| 5,906,811 A | * | 5/1999 | Hersh | A61K 8/678 424/49 |
| 6,071,500 A | * | 6/2000 | Thistle | A61K 8/345 426/74 |
| 6,638,067 B2 | * | 10/2003 | Fischer | A61C 5/42 433/102 |
| 2005/0043400 A1 | | 2/2005 | Clarot | |
| 2010/0159037 A1 | | 6/2010 | Eustaquio | |

FOREIGN PATENT DOCUMENTS

DE 202008016832 * 4/2009

OTHER PUBLICATIONS

What is menthol? (American Lung Association, Accessed Dec. 29, 2021) (Year: 2021).*
Katiyar et al. (Microemulsions: a novel Drug Carrier System, Int. J. Pharm. Sci. Rev. Res., 20(2), May-Jun. 2013). (Year: 2013).*
Gröber et al., "Myth or Reality-Transdermal Magnesium?" Nutrients 9(8): 813 (2017) 8 pgs.
European Patent Office, International Search Report in International Application No. PCT/EP2019/050799 (dated Mar. 25, 2019).
European Patent Office, Written Opinion in International Application No. PCT/EP2019/050799 (dated Mar. 25, 2019).
International Bureau of WIPO, International Preliminary Report on Patentability in International Application No. PCT/EP2019/050799 (dated Jul. 14, 2020).
Anonymous, "Vitamin D3 Mouth Spray," Apr. 24, 2015 (Apr. 24, 2015), found in www.gnpd.com. abstract No. Database accession No. 3127033. Retrieved from: GNPD [online] MINTEL.

(Continued)

*Primary Examiner* — Melissa S Mercier
(74) *Attorney, Agent, or Firm* — Leydig, Voit & Mayer, Ltd.

(57) ABSTRACT

The invention relates to a food supplement containing minerals and/or vitamins, a humectant and, for example, essential oils. The food supplement is formulated as an oral spray. In particular, the invention relates to a concentrated food supplement in the form of an oral spray, containing a combination of magnesium ions, panthenol (vitamin B5), caffeine, menthol aroma and/or peppermint aroma, and a humectant. The food supplement is particularly suited for use in sport and in stressful situations.

2 Claims, No Drawings

(56) References Cited

OTHER PUBLICATIONS

Anonymous, "Vitamins Mouth Spray" May 15, 2008 (May 15, 2008), found in www.gnpd.com. abstract No. Database accession No. 910969. Retrieved from: GNPD [online] MINTEL.

* cited by examiner

FOOD SUPPLEMENT, USES THEREOF, METHOD FOR FOOD SUPPLEMENTATION, AND ORAL SPRAY

CROSS-REFERENCE TO RELATED APPLICATIONS

This patent application is the U.S. national phase of International Application No. PCT/EP2019/050799, filed on Jan. 14, 2019, which claims the benefit of German Patent Application No. 10 2018 200 492.7, filed Jan. 12, 2018 and German Patent Application No. 10 2018 205 160.7, filed Apr. 5, 2018, the disclosures of which are incorporated herein by reference in their entireties for all purposes.

The present invention relates to a food supplement that contains minerals and/or vitamins, a humectant, and, for example, essential oils. The food supplement is formulated as an oral spray here. The present invention in particular relates to a concentrated food supplement in the form of an oral spray containing a combination of magnesium ions, panthenol (vitamin B5), caffeine, menthol aroma and/or peppermint aroma, and a humectant. The food supplement is in particular suitable for use in sports and in strain situations.

The most various food supplements are known from the prior art. Concentrated forms are typically presented as powders. Known food supplements are portioned such that one unit, that is, e.g., a capsule, a powder sachet, an ampoule, etc., contains a single application amount of at least 15% of the recommended daily allowance of the vitamins and/or minerals.

There are furthermore also application types in the form of a concentrate that are e.g. filled in flasks of which then an aliquot is mixed with 50 to 100 ml of water before the application.

In physical and mental strain situations such as exams, presentations, speeches, or the like, a feeling of dryness in the mouth quickly becomes evident. One reason for this is that saliva production is controlled by the vegetative nervous system. During sports, the dryness of the mouth caused by mouth breathing additionally occurs.

The application of a food supplement formulated as a powder is in particular disadvantageous in the above-mentioned situations. The application of a powder in said situations is not only impractical, but also results in an unpleasant feeling due to the dryness of the mouth.

Starting from the previously cited prior art, it is therefore the object of the present invention to provide a food supplement that contains a combination of selected active ingredients (i) to support endurance activity or in strain situations in a highly concentrated manner; (ii) for long-lasting moisturizing of the lining of the mouth and of the pharyngeal area to avoid dryness of the mouth; and (iii) simultaneously to promote free deep breathing, which likewise has the effect of promoting concentration and enhancing performance. The active ingredients should be able to be simply resorbed by the body. The system can be transported comfortably, e.g. in a trouser pocket, and can be applied quickly.

The previously named object is achieved by the features of the independent claims. The respective dependent claims describe advantageous further developments of the invention.

In a first aspect, the present invention thus relates to a food supplement comprising or consisting of an aqueous solution or emulsion of a) at least one mineral selected from the group of minerals containing magnesium, potassium, calcium, iron, zinc, selenium, manganese, as well as mixtures and combinations thereof; and/or
b) at least one vitamin and/or at least one provitamin selected from the group consisting of pantothenic acid, dexpanthenol, vitamin B1, vitamin B2, vitamin B6, vitamin B12, vitamin C, vitamin E, niacin, folic acid, thiamine, riboflavin, biotin, as well as mixtures and combinations thereof;
c) at least one component for moisturizing and maintaining moisture of the oral mucosa and/or of the pharyngeal area (humectant); and
d) at least one component that promotes the feeling of free deep breathing preferably an essential oil (e.g. menthol oil and/or peppermint oil, menthol aroma and/or peppermint aroma and/or menthol and/or peppermint crystals, in the form of an oral spray.

The term "food supplement" in the sense of the present invention is understood here as defined by the Food Supplement Order (NemV) of May 24, 2004 (Federal Law Gazette I p. 1011), last amended by Article 11 of the Order of Wednesday, Jul. 5, 2017 (Federal Law Gazette I p. 2272) of the Federal Republic of Germany. A food supplement is accordingly a foodstuff that is intended to supplement the general diet;
a concentration of nutrients or other substances having a diet-specific or physiological effect alone or in a composition; and
is marketed in dosed form, in particular in the form of capsules, pastilles, tablets, pills, and other similar dosage forms, powder sachets, liquid ampoules, flasks with droplet dispensers, and similar dosage forms of liquids and powders for application in measured, small amounts.

In agreement with the Food Supplement Order, nutrients in the sense of the present invention are understood as vitamins and minerals, including trace elements.

The food supplements in accordance with the present invention thus represent a combination formulation comprising one or more components for food supplementation, i.e. important vitamins and/or minerals that have, e.g., a concentration promoting, stimulating, performance enhancing, anticonvulsant effect;
one or more components for a sustained, long-term moisturization of the mouth to eliminate dryness of the mouth triggered, e.g., by intensified breathing, in particular mouth breathing, for instance during sports, when giving speeches, etc., reduced saliva production controlled inter alia by the vegetative nervous system in situations of stress, strain, and anxiety;
one or more components that promote free and deep breathing (e.g., through the mouth and/or nose and pharyngeal area) and thereby have a strain reducing, focusing and performance enhancing effect.

It was surprisingly found that the effect of the performance enhancement, promotion of concentration, focusing, but also the overcoming of exhaustion and stress is substantially enhanced by the described combination in comparison with the application of the at least one vitamin and/or at least one mineral alone.

The formulation facilitates and activates free and deep breathing by a component such as methanol. The brain and also the muscles are consequently effectively provided with oxygen. The pleasing, cooling moisturization of the oral cavity additionally supports breathing and well-being. A dry mouth results in a nervous cough and unease.

It was surprisingly found that by application of the food supplement e.g. during sports, in stress situations, exam or anxiety situations, optimum performance conditions can be provided and that a focusing is possible and simultaneously an ideal application option is present. The food supplement supports the establishing of an enhanced mental and physical performance capability; a focusing, and concentration in stress, strain, and anxiety situations such as occurs in athletes, persons in exam and strain situations, key performers (e.g., executives, surgeons, etc.). At the same time, it contributes to an improvement in mental and physical well-being and to an optimization of physical parameters in, during and after stress situations and for rehabilitation. The formulation is therefore also suitable for relieving strain and stress and anxiety situations and for improving mental and physical wellbeing.

The formulation as an oral spray enables the administration of the food supplement as a spray or aerosol, in particular as a dosed puff having a predefined volume that can vary e.g. between 20 and 500 µm, preferably between 50 and 200 µl. The application as an oral spray allows the administration of the formulation in a plurality of very small amounts, also applied multiple times over the day. This portion-wise supply of the substances promotes an effective application and utilization. The active ingredients are preferably present in a highly concentrated from due to the application in very small amounts so that the at least 15% of the recommended daily allowance can be achieved with a few puffs. The formulation can nevertheless not be considered a concentrate in the conventional sense since no dilution takes place before application, but the formulation is rather applied directly from the spray system into the oral cavity in undiluted form. This also represents a challenge to the preparation of the highly concentrated formulation from a flavor aspect.

The active ingredients such as minerals and vitamins are thus resorbed faster and more effectively by the body through two intake paths: moving over the lining of the mouth directly into the blood and/or over the gastrointestinal tract.

This multiple application in a plurality of small doses distributed over the day increases the intake efficiency.

At the same time, the application as an oral spray enables a uniform wetting and distribution of at least one mouth moisturization component in the total oropharynx.

Essential components that e.g. promote free deep breathing accordingly also have an effect in the nasal area due to the application and distribution in the oropharynx since the pharynx represents the connection between the oral cavity and the nasal cavity. Such components consequently then promote the feeling of free deep breathing through the mouth and nose.

The formulation to be patented is, however, not only used for oral hygiene and oral care, as an oral deodorant and/or for dental hygiene and dental health maintenance.

It has surprisingly been found that the food supplement in accordance with the invention contributes to reducing fatigue, overtiredness, and exhaustion and has a stimulating, concentration promoting and performance enhancing effect. In addition, the food supplement eliminates dryness of the mouth or prevents it. It equally contributes to the electrolyte balance of the body, to normal muscle function, and to normal protein synthesis. Due to the formulation in accordance with the invention as an oral spray, a simple application is made possible in puffs during sports, when driving, or during an exam; the food supplement in accordance with the invention can e.g. be taken along in a trouser pocket/belt bag during sports.

The application of the active ingredients in volume-defined doses (i.e., in one or more puffs) is more effective than with a large amount supplied once. Unwanted side effects that some substances applied in high amounts cause are also avoided. The application can also be included perfectly into a training plan or into running training since the spray also contributes to oral moisturization and to better deep breathing.

The food supplement can either include at least one of the minerals named in feature a) and can be free of vitamins and/or provitamins named in feature b).

Alternatively, the food supplement can include at least one of the vitamins and/or provitamins named in feature b) and can be free of the minerals named in feature a).

It is equally possible that the food supplement includes at least one of the minerals named in feature a) and simultaneously one of the vitamins and/or provitamins named in feature b).

With the minerals a), it is preferred if the food supplement does not contain any further minerals except for said minerals a).

Alternatively, or additionally, it is equally preferred if the food supplement does not contain any further vitamins and/or provitamins except for said vitamins and/or provitamins b).

The disadvantages of the food supplements from the prior art, in particular when they are formulated as powders or drinking ampoules, can be avoided with the present invention. The application of the food supplement during sports in the form of a powder from a sachet and without liquid with an anyway dry mouth is more difficult for less pleasant than the application of a puff from an oral spray. The oral spray can be applied with one hand; both hands have to be used to open the sachet or to unscrew an ampoule. The substances can be administered in exactly dosed, small amounts (puffs) in portions spread over the day due to the application as an oral spray. This is in contrast to powders and drinking solutions in ampoules administered once a day that are not provided for a dose-controlled, portion-wise application. A portion-wise application, however, provides a better intake and utilization of the applied substances. Unwanted side effects of higher substance amounts applied once such as with magnesium that can cause stomach upsets and/or diarrhea can also be avoided with such a portion-wise application.

The present invention combines highly concentrated food supplement in liquid form with a component for the long-lasting moisturization of the oral and pharyngeal area and with a component that promotes breathing deeply through the mouth and nose. The food supplement in accordance with the present invention is thus ideally suitable for support in endurance sports activities and/or in physical or mental strain situations.

The food supplements contain the previously described components in concentrated, liquid form. The required daily amount of minerals and vitamins can thus be achieved by administration of exactly defined small liquid amounts, spread over the day, for example, portion-wise, in a few puffs of the food supplement formulated as an oral spray.

The minerals and vitamins and also the other active ingredients contained in the food supplement are thereby available faster. Magnesium or e.g. also caffeine (preferably 1 to 120 mg, more preferably 22 to 100 mg, particularly preferably 25 to 80 mg of caffeine in an application amount of 0.1 to 6 ml, preferably 0.5 to 5 ml, particularly preferably 1 to 4 ml) can thus in particular be supplied to the body fast when required.

The faster availability of the ingredients contained in the food supplement, in particular of the minerals, vitamins, provitamins, or further components, in particular takes place in the oral spray that is distributed and nebulized over a wide area in the oral cavity by two different application paths, namely:

applied over the gastrointestinal tract and over the lining of the mouth and moving directly into the blood from there.

The formulation in accordance with the invention of the food supplement effects a particularly advantageous and fast intake of the active ingredients contained in the food supplement since both of the previously named resorption mechanisms can be ideally utilized. The full potential of the present invention in particular develops on an application as an oral spray. Preferably contained substances that enhance viscosity further effect a muco-adhesive retention in the oral area and thus a further enhancement of the resorption rate.

In particular, the preferred combination of menthol, magnesium, and caffeine, optionally also pantothenic acid or dexpanthenol, in high concentration and of a humectant (e.g., glycerin) has a concentration and performance enhancing effect, influences both neuromuscular processes, has a muscle relaxing and anti-convulsant effect, enables free deep breathing, simultaneously eliminates dryness of the mouth, and promotes a long-lasting feeling of moisturization and freshness in the mouth.

The oral spray preferably contains the at least one mineral or the at least one vitamin and/or the at least one provitamin in a highly concentrated form. It is of advantage in this process if the at least one mineral a) and/or the at least one vitamin b) is/are each so concentrated that at least 15% and at most 140% of the recommended daily allowance in accordance with Annex 1 of the Directive 2008/100/EC of the Commission of Oct. 28, 2008 (Recommended Daily Allowance, "RDA") is applied portion-wise distributed over the day in a total application amount of 0.1 to 10 ml, preferably 0.5 to 8 ml, particularly preferably 1 to 4 ml, for the oral spray. The previously named figures for the RDA in accordance with the "Guidance Document for Competent Authorities for Control of Compliance with EU Legislation on Regulation (EU No. 1169/2011, Table 2) can differ by up to 50% and −20% and for minerals by +45% and −20%. Said amounts indications are here each with respect to the amount of the respective metal (that is the respective total amount of magnesium, potassium, calcium, iron, zinc, selenium, manganese) per se—independently of the kind of compound of this metal contained.

A preferred content of the at least one humectant here amounts to 0.01 to 15 wt. %, preferably 0.05 to 10 wt. %, particularly preferably 0.1 to 5 wt. %, with respect to the food supplement.

A first variant with respect to component d) that promotes the feeling of free deep breathing provides that it is selected from the group consisting of crystalline menthol, menthol oil, menthol aroma, and mixtures and combinations thereof.

It is preferred here that preferably 1 to 500 mg, preferably 20 to 400 mg, particularly preferably 50 to 250 mg of the previously named component d) is contained in an application amount of 0.1 to 10 ml, preferably 0.5 to 8 ml, particularly preferably 1 to 4 ml, for the oral spray of the formulation.

It is alternatively and equally preferred that component d) that promotes the feeling of free deep breathing can be selected from the group consisting of peppermint extract, peppermint oil, peppermint aroma, and mixtures and combinations thereof.

In this case, component d) is preferably 0.0003 to 30 mg, preferably 0.001 to 10 mg, particularly preferably 0.01 to 5 mg, in an application amount of 0.1 to 6 ml, preferably 0.5 to 5 ml, particularly preferably 1 to 4 ml.

It is, however, equally also possible that both a substance selected from the group consisting of crystalline menthol, menthol oil, menthol aroma, and mixtures and combinations thereof and a component selected from the group consisting of peppermint extract, peppermint oil, peppermint aroma, and mixtures and combinations thereof are contained as component d) in the food supplement. In this case that both the previously named substance groups are contained, the respective individual components are contained within the framework of the previously named preferred amount indications.

The minerals a) preferably contained—with the exception of selenium—in the food supplement are here in particular contained as inorganic or organic salts of said metal cations, in particular as acetates, carbonates, chlorides, citrates, gluconates, glycerophosphates, orthophosphates, lactates, hydroxides, hydrogen sulfates, and/or sulfates. Selenium is preferably contained as sodium selenite, sodium hydrogen selenite, and sodium selenate.

The at least one mineral is preferably selected from the group consisting of inorganic or organic magnesium salts, in particular magnesium acetate, magnesium carbonate, magnesium chloride, magnesium salts of citric acid, magnesium gluconate, magnesium glycerophosphate, magnesium salts of orthophosphoric acid, magnesium lactate, magnesium hydroxide, magnesium oxide, and/or magnesium sulfate. It can be possible here that the one or more of said magnesium salts represent the only mineral that is contained in the food supplement in accordance with the invention.

The previously named magnesium-based mineral is here contained in a corresponding amount that preferably contains 35 to 450 mg magnesium ions, preferably 40 to 250 mg magnesium ions, particularly preferably 50 to 100 mg magnesium ions, in an application amount of 0.1 to 6 ml, preferably 0.5 to 5 ml, particularly preferably 1 to 4 ml, for the oral spray or 3 to 30 ml, preferably 5 to 25 ml, particularly preferably 10 to 20 ml, for the drinking solution.

A preferably contained humectant is in particular selected from the group consisting of polyhydroxy compounds comprising sorbite, 1,2-propanediol, glycerin, cellulose derivatives such as carmellose (carboxymethylcellulose), methyl cellulose, hydroxy propylmethyl cellulose, and carbomers, and mixtures and combinations thereof.

The food supplement in accordance with the invention in particular contains dexpanthenol of which 0.5 to 15 mg is preferably contained in an application amount of 0.1 to 6 ml, preferably 0.5 to 5 ml, particularly preferably 1 to 4 ml, for the oral spray or 3 to 30 ml, preferably 5 to 25 ml, particularly preferably 10 to 20 ml, for the drinking solution.

To promote the stimulating effect and to enhance attentiveness, performance capability, and reaction capacity, caffeine can additionally be contained in the food supplement, preferably 10 to 120 mg, preferably 22 to 100 mg, particularly preferably 25 to 80 mg magnesium ions in an application amount of 0.1 to 6 ml, preferably 0.5 to 5 ml, particularly preferably 1 to 4 ml, for the oral spray.

It is furthermore advantageous if the food supplement contains at least one substance that enhances viscosity, in particular alginate, xanthan and/or gum arabic and/or glycosaminoglycans, e.g., hyaluronic acid and/or chondroitin sulfate as well as mixtures and combinations thereof, preferably in a concentration of 0.01 to 5 wt. %, particularly preferably of 0.1 to 1 wt. %.

The substances enhancing viscosity preferably contained in the food supplement promote an extended dwell time at the lining of the mouth and thus a more effective intake of the ingredients thanks to a film formation they cause. The oral spray is compact, is therefore easy to take along, is convenient, usable at any time by administering a puff into the open mouth, and can be easily applied by puffs, in particular during sports, during exams, or when driving.

Further additives possibly contained in the food supplement are in particular selected from the group consisting of emulsifiers such as polysorbates, sorbitan esters, and lecithins; oils, e.g. MCT oils; C-8 fatty acids (caprylic acid), C-10 fatty acids (capric acid) and mixtures thereof; carbohydrates, in particular glucose, fructose, dextrose, maltose, xylitol, and/or sorbitol; essential oils (e.g. lavender, orange, vanilla, jasmine, lemongrass, mandarin, citrus) and/or extracts, e.g. peppermint, orange, lemon, lime, blackcurrant (cassis), chokeberry, papaya, vanilla, aromas, e.g. vanillin aromas such as vanillin, bitter almonds, bitter masking aroma, citrus, lemongrass, ginger; sweeteners such as saccharin and its Na—, K— and Ca— salts (E 954), aspartame (E 951), acesulfame K (E 950), sucralose (E 955), thaumatin (E 957), steviolglycoside (E 960), aspartame acesulfame salt (E 962), and advantame (E 969); humectants; expectorants, e.g. essential oils or extracts of e.g. aniseed, licorice, primrose; buffers; complexing agents such as EDTA and/or citric acid, as well as auxiliary agents for food supplements, preferably in a concentration of 0.001 to 22 wt. %, further preferably of 1 to 21 wt. %, further preferably of 5 to 19%, particularly preferably 10 to 17 wt. %.

The presence of caffeine and/or a mood enhancing component such as e.g. extracts and/or essential oils can effectively additionally support and enhance alertness, concentration, and performance and can reduce strain, stress, and feelings of anxiety.

In a preferred embodiment, the food supplement contains only one single emulsifier, for example polysorbate 80, soya lecithin, or similar. Co-emulsifiers are not contained in this case.

A particularly preferred embodiment provides that at least one medium chain triglyceride (MCT oil) is contained in the food supplement and is selected from the group consisting of medium chain triglycerides (MCT oils), whose fatty acids are at least 90 mol % C-8 fatty acid (caprylic acid) and C-10 fatty acid (capric acid), e.g. 60-80 mol % C-8 fatty acid (caprylic acid) and 40-20 mol % C-10 fatty acid (capric acid); vegetable medium chain triglycerides (MCT oils), in particular MCTs on the basis of coconut oil and/or palm oil, and mixtures and combinations thereof, for example in the amounts previously named for the additives.

The food supplement in accordance with the present invention is in particular self-preserving and can thus be formulated without preservatives. An embodiment in particular provides a self-preserving formulation in that the food supplement is filled into a so-called airless aerosol or spray device. In the sense of the present invention, in this process preservatives usual for food supplements such as potassium sorbate, sorbinic acid, calcium sorbate, benzoic acid, sodium benzoate, potassium benzoate, calcium benzoate, 4-hydroxybenzoic acid ethyl ester, sodium-4-hydroxybenzoic acid ethyl ester, 4-hydroxybenzoic acid propyl ester, sodium-4-hydroxybenzoic acid propyl ester, 4-hydroxybenzoic acid methyl ester, sodium-4-hydroxybenzoic acid methyl ester, sulfur dioxide/sulfuric acid, sodium sulfite, sodium hydrogen sulfite, sodium disulfite, potassium disulfite, calcium sulfite, calcium hydrogen sulfite, potassium hydrogen sulfite, orthophenyl phenol, sodium orthophenyl phenol, nisin, natamycin, formic acid, sodium formiate, potassium formiate, urotropin, dimethyl dicarbonate, ethyl laurylarginate, potassium nitrite, sodium nitrite, sodium nitrate, potassium nitrate, acetic acid, potassium acetate, sodium acetate, sodium diacetate, calcium acetate, lactic acid, propionic acid, sodium propionate, calcium propionate, potassium propionate, boric acid, sodium tetraborate, carbon dioxide, malic acid, fumaric acid, and/or lysozyme are understood as preservatives in the sense of the present invention here. Free of preservatives here means that the named substances are contained in a concentration of less than 0.001 wt. %, related to the food supplement.

Alternatively, the food supplement can, however, also contain one or more of the previously named preservatives. Preferred preservatives are sorbic acid, potassium sorbate and/or calcium sorbate, with potassium sorbate being very particularly preferred.

The food supplement is further preferably free of cyclodextrins.

The emulsion underlying the food supplement can here be a microemulsion or a nanoemulsion.

The present invention additionally relates to the use of the food supplement in accordance with the invention for non-therapeutic food supplementation, in particular before, during, and/or after a sports activity, in stress situations, exam situations, and/or when driving.

The present invention further relates to a method of food supplementation in which a food supplement in accordance with one of the preceding claims is applied into the mouth of a person in the form of a spray, in particular before, during, and/or after a sports activity (e.g. an endurance sport, in particular cycling, running, e.g. marathons, skiing, or mountain climbing), in stress situations, in exam situations, in stress, strain and anxiety situations, on tiredness, lack of sleep, and/or exhaustion (e.g. in exam situations, when driving, e.g. professional truck drivers), to release strain and to improve mental and physical wellbeing.

On application of the spray, the food supplement is in particular atomized into the oral area and/or pharyngeal area of a person using a corresponding atomizer. The application preferably takes place several times a day here, in particular 3 to 50 times, further preferably 5 to 20 times, with in particular respectively 1 to 10 puffs @ 10 to 500 µl, preferably 50 to 200 µl, being applied.

The present invention further relates to a method of non-therapeutic refreshment, of non-therapeutic support of free deep breathing, of non-therapeutic performance enhancement, of non-therapeutic moisturization of the lining of the mouth, and/or of non-therapeutic reduction of tiredness and/or exhaustion in which a food supplement in accordance with the invention is applied into the mouth of a person in the form of a spray or is taken as a drinking solution. The use of the spray takes place here in accordance with the procedure presented above.

In addition, medical or therapeutic aspects of the food supplement in accordance with the present invention are described. The food supplement is in particular suitable for treating mucous obstructions; the food supplement is used as an expectorant here. The food supplement is furthermore suitable for use in the prevention and/or treatment of muscle cramps.

As with the non-therapeutic usage purposes, the food supplement is here also applied into the mouth of a person in the form of a spray. The application preferably takes place several times a day here, in particular 3 to 50 times, further preferably 5 to 20 times, with in particular respectively 1 to 10 puffs @ 10 to 500 μl, preferably 50 to 200 μl, being applied.

The present invention additionally relates to an oral spray comprising a storage container in which a food supplement in accordance with the invention is stored and to a spray head that is connected or connectable to the storage container and that enables an administration of the food supplement as a puff. The spray head can be designed as a pump head that is e.g. manually actuated by a user. Alternatively, the oral spray can also be configured such that the food supplement is pressurized in the storage container and independently flows out of the spray head on the actuation of the spray head. The pump spray can be configured as an airless system or as a non-airless system, with the design as an airless system being preferred.

The present invention was described in more detail with reference to the following exemplary formulation.

The food supplements of Examples 1 to 5 are in particular suitable for use in sports and in strain situations to enhance mental and physical performance capability can be used for these purposes.

The food supplements of Examples 6 to 8 are in particular suitable for releasing strain and stress and anxiety situations with a simultaneous improvement in wellbeing and in mental and physical performance capability and can be used for these purposes.

EXAMPLE 1

| | wt. [%] | mg/ml |
|---|---|---|
| Magnesium chloride hexahydrate | 14.0-15 | 145-150 |
| Maltodextrin | 2.0 | 20 |
| Dextrose | 1.0 | 10 |
| Glycerin | 1.0 | 10 |
| Caffeine | 1.0 | 10 |
| Dexpanthenol (optional) | 0.15-0.4 | 1.5-4.0 |
| Aspartame | 0.05 | 0.5 |
| Saccharin | 0.004 | 0.04 |
| MCT oils | 5.0 | 50 |
| Polysorbate 80 | 16 | 160 |
| Span 80 | 1.8 | 18 |
| Menthol, recryst. | 4.5 | 45 |
| Peppermint aroma | 0.15 | 1.5 |
| Menthol aroma | 0.02 | 0.2 |
| Oelum Menthae piperitae/Peppermint oil | 0.1 | 1 |
| Bitter masking aroma | 0.002 | 0.02 |
| Vanillin | 0.04 | 0.4 |
| Ethanol | ≤0.1 | ≤1.0 |
| Water | Ad 100 | Ad 1 |

EXAMPLE 2

| | wt. [%] | mg/ml |
|---|---|---|
| Magnesium chloride hexahydrate | 14.0-15 | 145-150 |
| Maltodextrin | 2.0 | 20 |
| Dextrose | 1.0 | 10 |
| Glycerin | 1.0-1.5 | 10-15.0 |
| Caffeine | 1.0-1.3 | 10-13 |
| Dexpanthenol (optional) | 0.15-0.4 | 1.5-4.0 |
| Aspartame | 0.03 | 0.3 |
| Saccharin | 0.004 | 0.04 |
| MCT oils | 5.0 | 50 |
| Polysorbate 80 | 16 | 160 |
| Menthol, recryst. | 4.5 | 45 |
| Peppermint aroma | 0.15 | 1.5 |
| Menthol aroma | 0.03 | 0.3 |
| Oelum Menthae piperitae/Peppermint oil | 0.1 | 1 |
| Bitter masking aroma | 0.005 | 0.05 |
| Vanillin | 0.05 | 0.5 |
| Ethanol | ≤0.1 | ≤1.0 |
| Water | Ad 100 | Ad 1 |

EXAMPLE 3

| | wt. [%] | mg/ml |
|---|---|---|
| Dextrose | 2.0-10 | 20-100 |
| Glycerin | 1.0-3.0 | 10-30 |
| Caffeine | 1.0-1.5 | 10-15 |
| Vitamin B1 (optional) | 0.005-0.006 | 0.05-0.06 |
| Vitamin B2 (optional) | 0.006-0.008 | 0.06-0.08 |
| Vitamin B12 (optional) | 0.0005- | 0.005 |
| Niacin (optional) | 0.4-0.6 | 4-6 |
| Dexpanthenol | 0.15-0.4 | 1.5-4.0 |
| Aspartame | 0.03 | 0.3 |
| Saccharin | 0.004 | 0.04 |
| MCT oils | 1.0-5.0 | 10-50 |
| Polysorbate 80 | 2-12 | 20-120 |
| Menthol, recryst. | 0.5-4.5 | 5-45 |
| Peppermint aroma | 0.05-0.15 | 0.5-1.5 |
| Menthol aroma | 0.003-0.03 | 0.03-0.3 |
| Oelum Menthae piperitae/Peppermint oil | 0.001-0.1 | 0.01-1.0 |
| Vanillin | 0.001-0.05 | 0.01-0.5 |
| Ethanol | ≤0.1 | ≤1.0 |
| Water | Ad 100 | Ad 1 |

EXAMPLE 4

| | wt. [%] | mg/ml |
|---|---|---|
| Magnesium hydrogen citrate | 15.0-16 | 150-160 |
| Maltodextrin | 1.0 | 10 |
| Dextrose | 10.0 | 100 |
| Glycerin | 1.0-1.5 | 10-15.0 |
| Caffeine | 1.0-1.3 | 10-13 |
| Dexpanthenol (optional) | 0.15-0.4 | 1.5-4.0 |
| Vitamin B1 (optional) | 0.005-0.006 | 0.05-0.06 |
| Vitamin B2 (optional) | 0.006-0.008 | 0.06-0.08 |
| Vitamin B12 (optional) | 0.0005 | 0.005 |
| Niacin (optional) | 0.4-0.6 | 4-6 |
| Aspartame | 0.03 | 0.3 |
| Saccharin | 0.004 | 0.04 |
| MCT oils | 5.0 | 50 |
| Polysorbate 80 | 10- | 100-160 |
| Menthol, recryst. | 4.5 | 45 |
| Peppermint aroma | 0.15 | 1.5 |
| Menthol aroma | 0.03 | 0.3 |
| Oelum Menthae piperitae/Peppermint oil | 0.1 | 1 |
| Bitter masking aroma | 0.005 | 0.05 |
| Aniseed oil (optional) | 0.005-0.1 | 0.05-1 |
| Vanillin | 0.05 | 0.5 |
| Ethanol | ≤0.1 | ≤1.0 |
| Water | Ad 100 | Ad 1 |
| Set pH with NaOH to pH 5-6 | | |

EXAMPLE 5

| | wt. [%] | mg/ml |
|---|---|---|
| Magnesium chloride hexahydrate | 30.0-37.0 | 300-370 |
| Maltodextrin (optional) | 0.1-2.2 | 1.0-22 |
| Dextrose | 0.8-1.2 | 8.0-12 |
| Glycerin | 0.5-1.2 | 5.0-12 |
| Caffeine | 0.8-1.2 | 8.0-1.2 |
| Dexpanthenol (optional) | 0.15-0.40 | 1.5-4.0 |
| Vitamin B1 (optional) | 0.005-0.006 | 0.05-0.06 |
| Vitamin B2 (optional) | 0.006-0.008 | 0.06-0.08 |
| Vitamin B12 (optional) | 0.0003-0.0007 | 0.003-0.007 |
| Niacin (optional) | 0.4-0.6 | 4.0-6.0 |
| Aspartame | 0.04-0.06 | 0.4-0.6 |
| Saccharin | 0.005-0.007 | 0.05-0.07 |
| MCT oils from 100% C-8 fatty acids (caprylic acid) and C-10 fatty acids (capric acid). | 4.0-6.0 | 40-60 |
| Polysorbate 80 (Lamsorb SMO 20) | 12-20 | 120-200 |
| Menthol, recryst. | 3.0-6.0 | 30-60 |
| Oelum Menthae piperitae/ Peppermint oil | 0.2-0.4 | 2.0-4.0 |
| Vanillin (optional) | 0.2-0.3 | 2.0-3.0 |
| 1,2 Propanediol | 0.25-0.40 | 2.5-4.0 |
| BHT and/or BHA | 0.0-0.05 | 0.3-0.5 |
| Potassium sorbate (optional) | 0.10-0.18 | 1.0-1.8 |
| Citric acid | 0.05-0.09 | 0.5-0.9 |
| Water | Ad 100 | Ad 1 |

EXAMPLE 6

| | mg/ml |
|---|---|
| MCT oil (consisting of 70% caprylic acid and 30% capric acid; possible traces of other fatty acids as contaminants) | 50.00 mg |
| Menthol, recryst. | 45.00 mg |
| Oelum Menthae piperitae | 3.00 mg |
| Vanillin | 2.50 mg |
| 1,2 Propanediol | 3.00 mg |
| Essential oils of blackcurrants (optional) | 0.2-5 |
| BHT | 0.2-0.4 mg |
| Polysorbate 80 | 160.00 mg |
| Glycerin | 10-12.00 mg |
| Citric acid | 0.4-0.70 mg |
| Magnesium chloride hexahydrate | 350.00 mg |
| Potassium sorbate (optional) | 0.04-1.40 mg |
| Caffeine | 10.00 mg |
| Maltodextrin | 18-20.00 mg |
| Dextrose | 9.00-10.00 mg |
| Aspartame | 0.50 mg |
| Saccharin | 0.06 mg |
| Water | ad 1 ml |

EXAMPLE 7

| | wt. [%] | mg/ml |
|---|---|---|
| Zinc-D gluconate 3 H2O | 0.012-0.040 (1.5 to 5 mg Zinc ion) | 0.12-0.4 |
| Glycerin | 0.5-1.5 | 5-15 |
| Pantothenic acid (Vit B5) | 0.15-0.4 | 1.5-4.0 |
| Caffeine (optional) | 0.5-1.0 | 5-1 |
| Dextrose | 0.1-1.5 | 1-15 |
| Sorbitol (optional) | 0.2-3.5 | 2-35 |
| Polysorbate 80 | 3.0-16.0 | 30-160 |
| MCT oil | 1.0-5.0 | 10-50 |
| Menthol, recryst. | 0.2-4.5 | 2-35 |
| Essential oils of blackcurrants (Optional) | 0.05-1 | 0.5-10 |
| Lavender oil (Lavandula Angustifolia) (Optional) | 0.2-3.0 | 2-30 |
| Vanillin (optional) | 0.1-0.25 | 2.5 |
| Potassium sorbate (optional) | 0.4-14 | 0.04-1.40 |
| Citric acid/NaOH | For pH setting to pH 6.0-pH 7.0 | |

EXAMPLE 8

| | wt. [%] | mg/ml |
|---|---|---|
| Zinc-D gluconate 3 H2O | 0.012-0.040 (1.5 to 5 mg Zinc ion) | 0.12-0.4 |
| Glycerin | 0.5-1.5 | 5-15 |
| Pantothenic acid (Vit B5) | 0.15-0.4 | 1.5-4.0 |
| Caffeine (optional) | 0.5-1.0 | 5-1 |
| Dextrose | 0.1-1.5 | 1-15 |
| Sorbitol (optional) | 0.2-3.5 | 2-35 |
| Polysorbate 80 | 3.0-16.0 | 30-160 |
| MCT oil | 1.0-5.0 | 10-50 |
| Menthol, recryst. | 0.2-3.0 | 2-35 |
| Peppermint oil (Oleum menthae pipertae) (optional) | 0.05-0.3 | |
| Orange oil | 0.2-3.0 | 2-30 |
| Vanillin (optional) | 0.1-0.25 | 2.5 |
| Potassium sorbate (optional) | 0.4-14 | 0.04-1.40 |
| Citric acid/NaOH | For pH setting to pH 6.0-pH 7.0 | |

The invention claimed is:

1. A food supplement which has the following composition:

| | mg/ml |
|---|---|
| MCT oil (consisting of 70% caprylic acid and 30% capric acid; possible traces of other fatty acids as contaminants) | 50.00 mg |
| Menthol, recryst. | 45.00 mg |
| Oelum Menthae piperitae | 3.00 mg |
| Vanillin | 2.50 mg |
| 1,2 propanediol | 3.00 mg |
| BHT | 0.2-0.4 mg |
| Polysorbate 80 | 160.00 mg |
| Glycerin | 10-12.00 mg |
| Citric acid | 0.4-0.70 mg |
| Magnesium chloride hexahydrate | 350.00 mg |
| Potassium sorbate (optional) | 0.04-1.40 mg |
| Caffeine | 10.00 mg |
| Maltodextrin | 18-20.00 mg |
| Dextrose | 9.00-10.00 mg |
| Aspartame | 0.50 mg |
| Saccharin | 0.06 mg |
| Water | ad 1 ml. |

2. A method for providing non-therapeutic food supplementation to a person in need thereof, the method comprising applying a food supplement in accordance with claim 1 into the mouth of the person.

* * * * *